United States Patent [19]

van Andel

[11] Patent Number: Plant 7,748

[45] Date of Patent: Dec. 10, 1991

[54] CARNATION NAMED STABARGAR

[75] Inventor: Jacob van Andel, Aalsmeer, Netherlands

[73] Assignee: Van Staaveren B.V., Aalsmeer, Netherlands

[21] Appl. No.: 549,802

[22] Filed: Jul. 9, 1990

[51] Int. Cl.[5] ..... A01H 5/00

[52] U.S. Cl. ..... Plt./73

[58] Field of Search ..... Plt./70, 73

*Primary Examiner*—Howard J. Locker

*Attorney, Agent, or Firm*—Charles W. Rummler

[57] ABSTRACT

A new and original mini-spray carnation variety particularly distinguished by the Tyrian purple coloration of its small blossoms, which are borne in a cluster and are produced intermittently during the Spring, Summer, and Fall blooming periods. The plant itself has a vigorous, upright growth habit and a height of about 60 cm.

1 Drawing Sheet

BACKGROUND OF THE NEW PLANT

This new mini-spray carnation cultivar originated as a hybrid seedling developed by me in 1980 at our nursery in Aalsmeer, Holland by crossing two varieties selected from our collection of carnations maintained for breeding purposes at Aalsmeer. This particular seedling was selected for propagation because of its unusual Tyrian purple flower coloration and the overall high quality of the plant. Asexual propagation of this selected plant was done by means of cuttings under my direction at Aalsmeer. Propagation of this new plant by cuttings continued from generation to generation to determine whether the novel characteristics of the selected seedling would be retained from generation to generation and its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of spray stems with buds and flowers, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S. Colour Chart published by the Royal Horticultural Society of London, England.

THE PLANT

Origin: Seedling.

Parentage:

*Seed parent.*—85274-1C (unpatented).

*Pollen parent.*—D. Barbatus (unpatented).

Classification:

*Botanic.*—Dianthus Hybrid.

*Commercial.*—Mini-spray carnation.

Form: Strong, upright bush with hardly any shoots in the flower stem nodes.

Height: 60 cm, in average.

Main stem:

*Length.*—In average, about 50 cm.

*Growth.*—Vigorous and upright.

*Branching character.*—Hardly any shoots in the flower stem nodes.

Foliage:

*Number of leaves.*—Varies with the season or amount of daylight.

*Leaf size.*—About 150 mm long and 12 mm wide at the fifth node.

*Leaf shape.*—Elliptical and curled. Margins: Entire. Texture: Leathery. Color: Both upper and under sides are dark green.

THE BUD

Size: Small.

*Diameter.*—Averaging about 10 mm.

*Length.*—Averaging about 20 mm.

Shape: Cylindrical.

Calyx:

*Shape.*—Cylindrical.

*Size.*—Averaging about 10 mm in width and 20 mm in length.

*Splitting.*—The calyx does not split.

*Aspect.*—Smooth.

Flower stem:

*Character.*—Sturdy and erect.

*Color.*—Dark green.

*Length.*—Averaging about 50 cm.

THE FLOWER

Blooming habit: Intermittent, during Spring to Fall blooming seasons.

Size of flower: Small.

*Diameter.*—Averaging about 30 mm.

*Depth.*—Averaging 8 to 10 mm.

Borne: On the umbel-like stems of a cluster.

Shape when first opening: Flat.

When mature: Becoming slightly rounded.

Petalage:

*Number of petals.*—Relatively few.

*Texture.*—Soft.

*Appearance.*—Velvety.

*Color*—Upper Sides: Both outer petals and inside petals: Body: 57A. Base: White. Reverse side: 63A.

Flower stem:

*Length.*—Averaging about 50 cm.

*Character.*—Strong and upright.

Discoloration:

*After full bloom.*—Color becomes darker.

Persistence: The flowers hang on and dry.

Disease resistance: Resistant to *Fusarium oxysporum.*

Lasting quality: Averaging about 14 days as a cut flower and 21 days on the plant.

REPRODUCTIVE ORGANS

Stamens:

*Number.*—Very few.

*Arrangement.*—Petaloid.

*Anthers.*—Size: Small. Color: Purple.

*Filaments.*—Length: About 25 mm. Color: White.

Pistils:

*Number.*—1.

*Styles.*—Length: About 20 mm. Color: White.

Stigmas:

*Color.*—Violet.

I claim:

1. The new and distinctive carnation plant, substantially as herein shown and described, particularly characterized by the Tyrian purple coloration of its flowers, its vigorous growth habit and the intermittent profuse production of flowers on strong and upright stems.

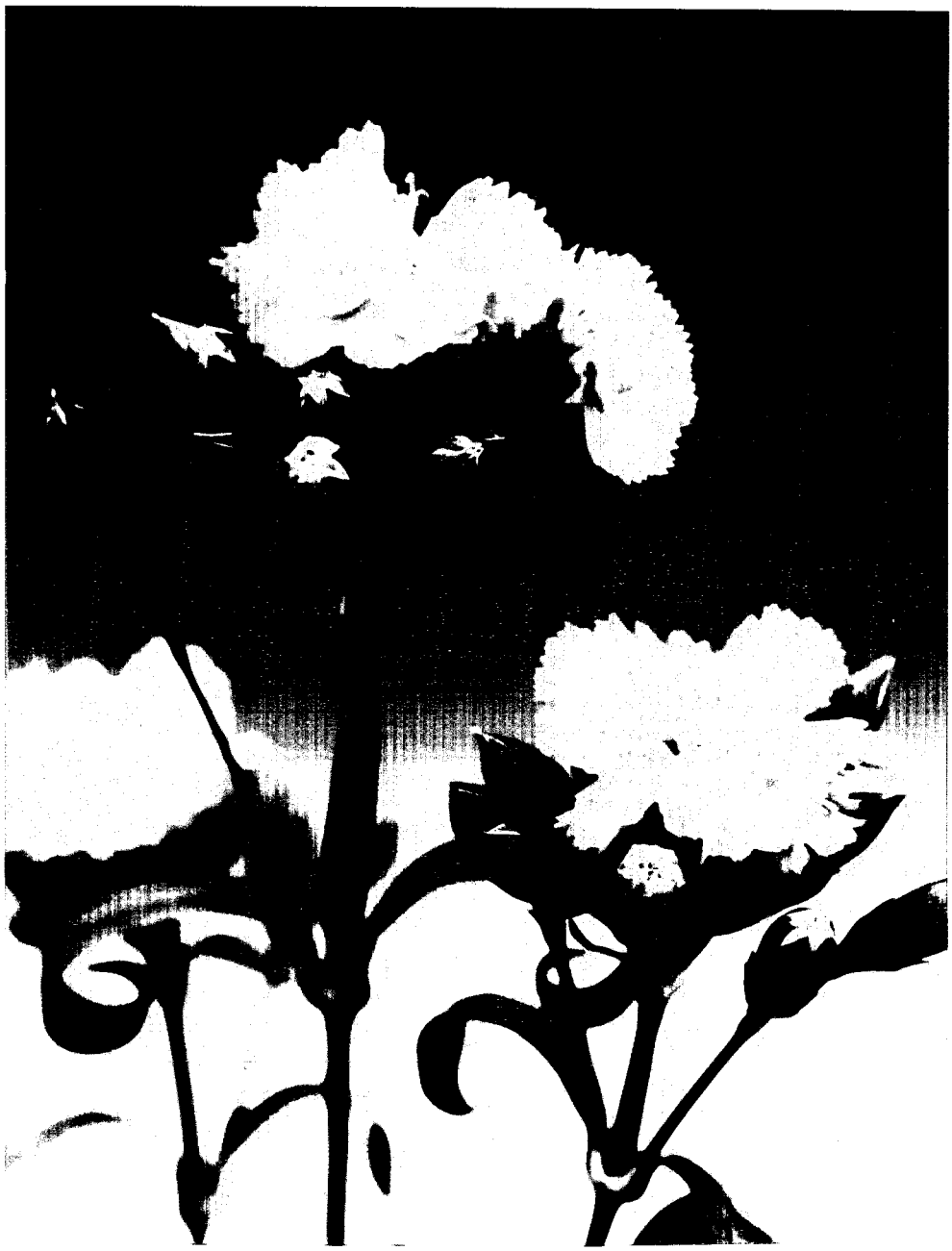

* * * * *